(12) United States Patent
Dams

(10) Patent No.: US 6,201,122 B1
(45) Date of Patent: Mar. 13, 2001

(54) FLUOROALIPHATIC RADICAL-CONTAINING ANIONIC SULFONAMIDO COMPOUNDS

(75) Inventor: Rudolf J. Dams, Antwerp (BE)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 07/986,648

(22) Filed: Dec. 8, 1992

(51) Int. Cl.[7] .......... C07C 311/09; C07D 241/04
(52) U.S. Cl. .......... 544/383; 560/150; 562/106; 562/556
(58) Field of Search .......... 560/150; 562/106, 562/556; 544/383

(56) References Cited

U.S. PATENT DOCUMENTS

| | | | |
|---|---|---|---|
| 2,759,019 | 8/1956 | Brown et al. | 260/556 |
| 2,809,990 | 10/1957 | Brown | 260/556 |
| 3,536,749 | * 10/1970 | Groves | 560/150 |
| 4,009,167 | * 2/1977 | Greenwald | 544/383 |
| 4,014,926 | * 3/1977 | Dear et al. | 562/105 |
| 4,069,244 | * 1/1978 | Mueller | 562/556 |
| 4,102,916 | 7/1978 | Falk | 260/458 |
| 4,484,990 | 11/1984 | Bultman et al. | 204/106 |
| 4,820,820 | * 4/1989 | Sebag et al. | 544/383 |
| 4,857,644 | * 8/1989 | Abou-Gharbia | 544/383 |

FOREIGN PATENT DOCUMENTS

| | | |
|---|---|---|
| 1346644 | 2/1974 | (GB) . |
| WO-A-90/03966 | 4/1990 | (WO) . |

OTHER PUBLICATIONS

"Organofluorine Compounds and their Industrial Applications," R.E. Banks, editor, pp. 218–226 Ellis Horwood, Ltd., (1979).

Product Information, Fluorad™ Fluorochemical Surfactants, 3M Bulletin 98–0211–2213–4 (38.3) BPH (1982).

* cited by examiner

Primary Examiner—Richard L. Raymond
(74) Attorney, Agent, or Firm—Robert H. Jordan

(57) ABSTRACT

Novel fluoroaliphatic radical-containing anionic sulfonamido compounds, methods of preparation and methods of use, including use as surfactants, are disclosed. Said compounds are conveniently prepared by the Michael addition of a fluoroaliphatic radical-containing compound to an ethylenically unsaturated compound.

15 Claims, No Drawings

FLUOROALIPHATIC RADICAL-CONTAINING ANIONIC SULFONAMIDO COMPOUNDS

This invention relates to fluoroaliphatic radical-containing sulfonamido compounds, a process for their preparation, and methods for using them as surfactants.

Certain fluoroaliphatic radical-containing compounds, or fluorochemicals, are useful as surfactants for a variety of demanding industrial applications. Their unique combination of properties are due mainly to the properties of the fluoroaliphatic radical: low surface energy, high chemical stability, and oleophobic-hydrophobic character. Because of these properties, fluorochemical surfactants are often useful in applications where conventional hydrocarbon surfactants, that is, relatively fluorine-free surfactants, do not perform adequately. For example, compared with hydrocarbon surfactants, fluorochemical surfactants (1) give much lower surface tension in aqueous systems, (2) are effective at much lower concentration, (3) show better stability in hostile environments (e.g., strong acids or bases, reducing or oxidizing media), and (4) exhibit surface activity in organic solvents systems, e.g., as a leveling agent in organic coatings. See, for example, "Organofluorine Compounds and their Industrial Applications", R. E. Banks, editor, pages 218–226, Ellis Horwood, Ltd., (1979).

Many fluorochemicals useful as surfactants are described in patents. U.S. Pat. No. 3,536,749 (Groves) describes the preparation of certain adducts from the reaction of certain fluorocarbon amides with an ester of acrylic acid or methacrylic acid. Adducts of the formula $R_fSO_2N(R)CH_2CH(R')CO_2R''$ are disclosed where $R_f$ is a perfluoroalkyl group containing from 3 to 18 carbon atoms, R' is hydrogen or methyl, and R" is an alkyl group containing up to 18 carbon atoms. Specific adducts prepared include $C_8F_{17}SO_2N(C_2H_5)CH_2CH_2CO_2C_2H_5$ and $C_5F_{11}CONHCH_2CH_2CO_2C_2H_5$.

U.S. Pat. No. 4,014,926 (Dear et al.) discloses certain compounds said to be useful as surfactants and as leveling agents in floor polish formulations. The invention is directed to fluorinated alkylamido sulfonic acids and salts of the formula $[R_f—R_6—SCH_2C(R_1)HC(O)NH—C(R_2)(R_3)—C(R_4)(R_5)—SO_3]_nM$, where $R_f$ is straight or branched chain perfluoroalkyl of 1 to 18 carbon atoms or perfluoroalkyl substituted by perfluoroalkoxy of 2 to 6 carbon atoms, $R_1$ is hydrogen or lower alkyl and each of $R_2$, $R_4$ and $R_5$ is individually hydrogen or a hydrocarbon radical, and $R_6$ is alkylene, alkylenethioalkylene, alkyleneoxyalkylene or alkyleneiminoalkylene with a secondary or tertiary nitrogen atom, $R_3$ is hydrogen, alkyl, aryl or pyridyl, M is hydrogen, a monovalent alkali metal, an alkaline earth metal, an organic base or ammonium, and n is an integer corresponding to the valency of M. A specific example is $C_6F_{13}CH_2CH_2SCH_2CH_2C(O)NHC(CH_3)_2CH_2SO_3K$.

U.S. Pat. No. 4,069,244 (Mueller) discloses certain fluorinated compounds, said to be useful as surfactants, of the formula $R_f—R^1—S—(CH_2)_y—CH(—COOH)—CH_2—CO—XQ$, where $R_f$ is a perfluoroalkyl group, $R^1$ is a branched or straight chain alkylene, alkylenethioalkylene, alkyleneoxyalkylene or alkyleneiminoalkylene group, X is oxygen or —NR, Q is an organic group containing at least one amino group and y is zero or 1. An example of a compound which was prepared is $C_8F_{17}CH_2CH_2SCH(COO^-)—CH_2CONH(CH_2)_3N^+H(CH_3)_2$.

U.S. Pat. No. 4,102,916 (Falk) discloses certain compounds, said to be useful as surfactants, having the formula $R_fR_1SCH_2CH(R_2)CONN(R_3)(R_4)(R_5)$ wherein $R_f$ is a perfluoroalkyl, $R_1$ is alkylene, oxy or thioalkylene, or alkyleneiminoalkylene; $R_2$ is hydrogen or alkyl; $R_3$ and $R_4$ are alkyl or together with nitrogen form a heterocyclic ring and $R_5$ is alkyl which may contain hydroxyl or carboxyl groups or an anionic function such as sulfonate, sulfate or carboxylate. A specific compound of the invention has the formula $C_6F_{13}CH_2CH_2SCH_2CH(CH_3)CONN(CH_3)_2CH_2CH(OH)CH_3$.

U.S. Pat. No. 2,759,019 (Brown, et al.) discloses certain perfluoroalkane-sulfonamidopolymethylenedialkylamine compounds and their corresponding quaternary ammonium derivatives. Such derivatives include $C_8F_{17}SO_2NHC_2H_4N^+(C_2H_5)_2(CH_3)\ CH_3SO_4^-$.

U.S. Pat. No. 2,809,990 (Brown) discloses certain fluorocarbon acids and derivatives. In particular, Brown discloses certain perfluoroalkane sulfonamido alkylenemonocarboxylic acids. Certain methods for making these compounds and their derivative are also disclosed. Such compounds include $C_8F_{17}SO_2NHCH_2CH_2CO_2H$.

Briefly, in one aspect, this invention provides novel fluoroaliphatic radical-containing sulfonamido compounds each of which comprises a fluoroaliphatic radical-containing sulfonamido group and an ethylenecarbonyl group whose beta ethylene carbon atom is bonded to a sulfur or nitrogen atom bonded to a linking group that is bonded to the nitrogen atom of said sulfonamido group. The carbonyl carbon atom of said ethylenecarbonyl group is bonded to an anionic hydrophilic polar group, comprising at least one atom selected from the group consisting of carbon, sulfur, oxygen, and nitrogen atoms. As used herein, "anionic" means those groups or compounds which can form anions when in aqueous mixtures. The compounds of this invention are useful as anionic surfactants.

Representative fluoroaliphatic radical-containing compounds useful in this invention include:

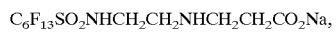

This invention also provides methods for the preparation of fluoroaliphatic radical-containing sulfonamido compounds by a Michael addition reaction.

And, this invention also provides methods for using the fluoroaliphatic radical-containing sulfonamido compounds of this invention as anionic surfactants in improving or imparting properties to solutions and substrates such as wetting, penetration, spreading, leveling, foam stabilization, flow properties, emulsification, and dispersability.

A class of the fluoroaliphatic radical-containing sulfonamido compounds of this invention can be represented by Formula I,

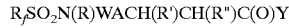

where $R_f$ is a fluoroaliphatic radical; A is S or NR'''; W is a linking group and is alkylene, siloxylene, silylene, arylene, or combinations thereof; R, R', R", and R''' are hydrogen, lower alkyl with, for example, 1 to 6 carbon atoms, aryl such as phenyl, or combinations thereof such as alkaryl, and can be functional groups, e.g., —$CH_2CH_2OH$ or —$CH_2CO_2NH_4$; Y is an anionic hydrophilic polar group which comprises at least one carbon, sulfur, oxygen, or nitrogen atom. In Formula I, A can be a secondary or tertiary, but not a quaternary, nitrogen atom. And, R and R''', together with the nitrogen atoms to which they are bonded and W, can form a ring, e.g. a substituted piperazine ring.

The fluoroaliphatic radical, $R_f$, is a stable, inert, preferably saturated, non-polar, monovalent aliphatic radical. It can be straight chain, branched chain, cyclic, or combinations thereof. It can contain catenary hetero-atoms, bonded only to carbon atoms, such as oxygen, divalent or hexavalent sulfur, or nitrogen. It is preferably a fully-fluorinated radical, but hydrogen or chlorine atoms can be present as substituents if not more than one atom of either is present for every two carbon atoms. The fluoroaliphatic radical has at least 3 carbon atoms, preferably 3 to 20 carbon atoms and most preferably about 4 to about 10 carbon atoms, and preferably contains about 40% to about 78% fluorine by weight, more preferably about 50% to about 78% fluorine by weight. The terminal portion of the fluoroaliphatic radical is a perfluorinated moiety which will preferably contain at least 7 fluorine atoms, e.g., $CF_3CF_2CF_2$—, $(CF_3)_2CF$—, $F_5SCF_2$—, or the like. The preferred fluoroaliphatic group is fully or substantially fluorinated and is preferably a perfluorinated aliphatic radical of the formula —$C_nF_{2n+1}$ where n is from 3 to 20.

The linking group W can be, for example, —$CH_2CH_2$—, —$CH_2CH_2$—$N(H)$—$CH_2CH_2$—, —$CH_2CH_2OCH_2CH$—$_2$, —$C_6H_4$—, —$CH_2CH_2CH_2Si(CH_3)_2[O$—$Si(CH_3)_2]_4$—$CH_2CH_2CH$—$_2$, and combinations thereof.

The anionic hydrophilic polar group, Y in Formula I, is a group which can form anions in aqueous mixtures, eg., —$NH(CH_2)_xCOOM$ or —$NH(CH_2)_xSO_3M$, where M is hydrogen, or a metal or ammonium ion, and x has a value of 1 to about 20.

The compounds of this invention can be prepared by a Michael addition reaction of a precursor fluoroaliphatic radical-containing sulfonamido compound which contains an active hydrogen atom with an ethylenically unsaturated compound which contains an electron-withdrawing group. This Michael addition can be illustrated by Scheme I.

Scheme I

In Scheme I, $R_f$, W, A, R, R', and Y are as defined above for Formula I.

Representative examples of the precursor fluoroaliphatic radical-containing sulfonamido compounds useful in the preparation of the compounds of this invention include:

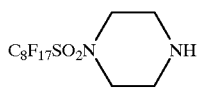

$C_8F_{17}C_2H_4SO_2NHCH_2CH_2NH_2$
$C_8F_{17}SO_2NHC_2H_4NH_2$
$C_8F_{17}SO_2N(C_2H_5)C_2H_4SH$
$C_4F_9SO_2NHC_3H_6Si(CH_3)_2OSi(CH_3)_2C_3H_6NH_2$
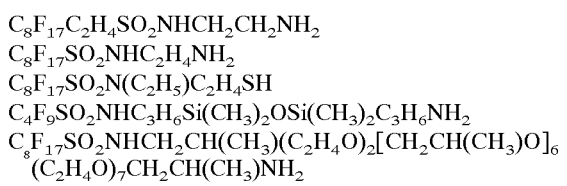
$C_8F_{17}SO_2N(C_2H_5)CH_2CH(OH)CH_2NH_2$ U.S. Pat. Nos. 2,803,656 (Ahlbrecht), 2,567,011 (Diesslin), and 3,419,595 (Hansen) have descriptions of synthetic routes to these precursor compounds, which descriptions are incorporated herein by reference.

Representative examples of unsaturated compounds useful in the preparation of the compounds of this invention by Michael addition include acrylic acid and its salts; maleic, fumaric and itaconic acids, their salts, anhydrides, and esters; acrylamide; N-substituted acrylamide such as N-propylacrylamide; acrylamides derived from amino-terminated polyethers (such as Jeffamine™ polyethers from Texaco) or amino-terminated poly(dimethylsiloxane) polymers; acrylonitrile; acrylic acid esters such as methyl, ethyl and dodecyl acrylates; acrylic acid esters of polyethyleneglycol (e.g. Carbowax™ from Union Carbide) or methoxy polyethyleneglycol; acrylic acid esters of hydroxy group containing block copolymers of ethylene oxide and propylene oxide (available as Pluronics™ from BASF) acrylic acid esters of poly(tetramethylene oxide) glycols (available as Theratane™ from DuPont); and acrylates of poly (dimethylsiloxane) polyols (available from Dow Corning). Functionalized unsaturated compounds can also be used including N-methylol acrylamide, diacetone acrylamide, 2-hydroxy-3-chloro-propyl acrylate, hydroxy acrylates such as hydroxyethyl acrylate, N-cyanoethyl acrylamide, vinylsulfonic acid and its salts, 2-acrylamido-2-methylpropanesulfonic acid (AMPS) and its salts.

The Michael addition reaction can be carried out in solvent or without solvent (neat). Suitable solvents include alcohols such as methanol, ethanol, and isopropyl alcohol, ethers such as ethyleneglycol, dimethylether, and tetrahydrofuran, ketones such as acetone and methyl ethyl ketone, N-methylpyrrolidinone, N,N-dimethylformamide, acetonitrile, trichloromethane, and toluene. Water can also be used, particularly in combination with the above polar solvents. The reaction temperature can range between room temperature and about 200° C. The addition reactions illustrated in Scheme I may be run at room temperature or with mild heating, for example 20 to 80° C. The conversion to the Michael adducts is generally very high, i.e. greater than 90%. To accelerate the addition reactions and to obtain higher conversions, a basic catalyst can be employed, such as triethylamine, pyridine, benzyltrimethylammonium hydroxide, and potassium hydroxide.

The fluoroaliphatic radical-containing sulfonamido compounds of this invention are useful as anionic surfactants for improving or imparting properties to aqueous and non-aqueous (organic) liquid systems such as wetting, penetration, spreading, leveling, foaming, foam stabilization, flow properties, emulsification, dispersability, and oil, water, and soil repellency. Said liquid system generally will comprise a liquid phase (in which the compound will be dissolved or dispersed) and one or more other phases selected from the group consisting of another liquid phase, a gas phase, and a phase of dispersed solids (e.g. polymer solids), and the system can be in the form of a solution, emulsion, suspension, or foam (such as an air foam). Examples of such liquid systems, or application areas for said compounds are rinsing, cleaning, etching, and plating baths, floor polish emulsions, photographic processes, water base coatings, solvent based coatings, fire fighting foams, lacquers, alkaline cleaners, fluoropolymer emulsions, soldering systems, and specialty inks, such as described, for example, in 3M Bulletin 98-0211-2213-4 (38.3) BPH.

The compounds of this invention useful as surfactants also can be incorporated into or mixed with other substances. For example, if sufficiently thermally stable, they can be incorporated into polymeric materials, such as polyamides, e.g. nylon, or polyolefins, e.g. polypropylene, which are cast, blown, extruded, or otherwise formed into shaped articles, such as films and fibers, the so-incorporated fluorochemicals modifying the properties of the shaped articles, such as the oil and water repellency of their surfaces. The compounds of this invention can also be mixed with other surfactants.

Objects and advantages of this invention are illustrated in the Examples below.

EXAMPLES

In the following Examples and Comparative Examples, fluoroaliphatic radical-containing compounds were prepared. The surface tension of water and isopropyl alcohol solutions containing these compounds was measured using a du Nouy tensiometer. The foaming properties of these solutions were also evaluated by generating foam and measuring the foam volume and half life.

Example 1

In this example, a Michael adduct of a fluoroaliphatic radical-containing sulfonamido amine and the potassium salt of 2-acrylamido-2-methyl-propanesulfonic acid (AMPS) was prepared.

Into a three-necked, 500 mL flask, fitted with a stirrer, condenser, and thermometer, were placed 10.3 g (0.05 mole) AMPS, 3.6 g potassium carbonate and 80 g of dimethylformamide (DMF) solvent. After 15 minutes of stirring at room temperature, a clear, homogeneous solution was obtained. After warming this solution to 40° C., 27.7 g (0.05 mole) of N-ethyl perfluorooctanesulfonamidoethylamine, $C_8F_{17}SO_2NHC_2H_4NH_2$, was added. After a mild exotherm, the reaction mixture was heated to 65° C. for 3 hours to yield a clear, amber colored solution. Gas-liquid chromatography ("GLC") of a sample of the reaction mixture indicated that all of the amine had reacted. Proton nuclear magnetic resonance ("H-NMR") analysis was consistent with the structure of the product as $C_8F_{17}SO_2NHC_2H_4NHC_2H_4CONHC(CH_3)_2CH_2SO_3K$.

Examples 2–6, Comparative Examples C1–C3

The fluoroaliphatic radical-containing compounds shown in Table 1 were prepared following the procedure of Example 1 and using the various nucleophilic reactants and unsaturated reactants shown in Table 2. The reactants and solvent used for each Example are summarized in Table 3. The nucleophilic reactants A, B, C, and D were prepared by the reaction of $C_8F_{17}SO_3CH_2CH_3$ or $C_4F_9SO_3CH_2CH_3$ with the appropriate amine. The amine used to prepare nucleophilic reactant D was Jeffamine™ ED-900, available from Texaco, where a is about 15.5 and b is about 2.5. Unsaturated reactant G was Carbowax™ 750 acrylate, where n is about 17. Yield of Michael adduct was greater than 95% in each Example and Comparative Example. The structure of each adduct was confirmed by H-NMR spectroscopic analysis. The products of Comparative Examples C2 and C3 were quaternized with $(C_2H_5)_2SO_4$ and propane sultone, respectively.

TABLE 1

| Example | Structure of Addition Product |
|---|---|
| 2 | $C_8F_{17}SO_2NHC_2H_4NHC_2H_4COONa$ |
| C1 | $C_8F_{17}SO_2NHC_2H_4NHC_2H_4COO(C_2H_4O)_nOCH_3$ |
| C2 | $C_8F_{17}SO_2NHC_2H_4N^+H(C_2H_5)C_2H_4COOC_2H_4N^+(CH_3)_2C_2H_5$ $[(CH_3CH_2SO_4^-)_2]$ |

TABLE 1-continued

| Example | Structure of Addition Product |
|---|---|
| C3 | $C_8F_{17}SO_2NHC_2H_4N^+H(C_3H_6SO_3^-)$- $CH_2CH_3COOC_2H_4N^+(CH_3)_2C_3H_6SO_3^-$ |
| 3 | $C_8F_{17}SO_2N\overbrace{\phantom{xxxxx}}NC_2H_4CONHC(CH_3)_2CH_2SO_3K$ (piperazine ring) |
| 4 | $C_4F_9SO_2NH(CH_2)_3Si(CH_3)_2OSi(CH_3)_2(CH_2)_3NH$- $C_2H_4CONHC(CH_3)_2CH_2SO_3K$ |
| 5 | $C_8F_{17}SO_2NHCH(CH_3)CH_2(C_2H_4O)_a[CH_2CH(CH_3)O]_b$- $CH_2CH(CH_3)NHC_2H_4CONHC(CH_3)_2CH_2SO_3K$ |
| 6 | $C_8F_{17}SO_2N(C_2H_5)C_2H_4SCH(COONH_4)CH_2COONH_4$ |

TABLE 2

Nucleophilic Reactants

A   $C_8F_{17}SO_2NHC_2H_4NH_2$

B   $C_8F_{17}SO_2N\overbrace{\phantom{xxxxx}}NH$ (piperazine ring)

C   $C_4F_9SONHC_3H_6Si(CH_3)_2OSi((CH_3)_2)C_3H_6NH_2$
D   $C_8F_{17}SO_2NHCH_2CH(CH_3)CH_2(C_2H_4O)_a[CH_2CH(CH_3)O]_b$- $CH_2CH(CH_3)NH_2$
E   $C_8F_{17}SO_2N(C_2H_5)C_2H_4SH$

Alpha-Beta Unsaturated Reactants

F   $CH_2{=}CHCOONa$
G   $CH_2{=}CHCOO(C_2H_4O)_aOCH_3$
H   $CH_2{=}CHCOOC_2H_4N(CH_3)_2$
I   $CH_2{=}CHCONHC(CH_3)_2CH_2SO_3K$
J   $HOOCCH{=}CHCOOH$

TABLE 3

| Example | Reactants | Solvent |
|---|---|---|
| 1 | A and I | DMF |
| 2 | A and F | DMF/Water (80/20) |
| C1 | A and G | 1,2-dimethoxyethane |
| C2* | A and H | 1,2-dimethoxyethane |
| C3** | A and H | 1,2-dimethoxyethane |
| 3 | B and I | DMF |
| 4 | C and I | DMF |
| 5 | D and I | DMF |
| 6*** | E and J | isopropyl alcohol/water (50/50) |

*2 moles of ethyl sulfate per mole of Michael adduct was also added.
**2 moles propane sultone per mole of Michael adduct was also added.
***Neutralized with $NH_4OH$.

Comparative Example C4

The fluoroaliphatic surfactant $C_8F_{17}SO_2N(C_2H_5)$ $CH_2CO_2K$ was prepared from the corresponding ethyl ester as described in U.S. Pat. No. 2,809,990 (Brown), (example 1) except that the ethyl ester was treated with KOH instead of NaOH.

Comparative Example C5

Comparative Example C5 was prepared by the Michael addition of $C_8F_{17}SO_2N(C_2H_5)H$ to acrylic acid to produce $C_8F_{17}SO_2N(C_2H_5)CH_2CH_2CO_2H$. GLC analysis indicated about 20% unreacted starting material was present. The acid was then converted to the potassium salt.

Comparative Example C6

In a 1-L, three-necked flask, fitted with a condenser, stirrer, and thermometer were placed 263 g (0.5 mole) of $C_8F_{17}SO_2N(C_2H_5)H$, 15 g of triethylamine, 3 g of phenothiazine, 150 g toluene and 90 g (0.9 mole) of ethyl acrylate. The reaction mixture was stirred and heated at reflux (about 97° C.) for 16 hours to yield the known adduct $C_8F_{17}SO_2N(C_2H_5)C_2H_4COOC_2H_5$ in 97% yield as shown by H-NMR analysis. The adduct was isolated by stripping off the toluene solvent, triethyl amine and excess ethyl acrylate under water aspirator pressure.

In a 500 mL, three-necked flask, fitted as above, were placed 31.3 g (0.5 mole) of the known adduct and 50 g of isopropyl alcohol. The mixture was stirred and heated to 60° C. and a solution of 4.2 g of KOH in 30 g of water added over 30 minutes. Heating was continued at 70° C. for 16 hours. The reaction mixture was neutralized using 10% aqueous $H_2SO_4$, diluted to 20% solids with a solution of 70% by volume water and 30% by volume isopropyl alcohol and filtered to yield a solution containing $C_8F_{17}SO_2N(C_2H_5)C_2H_4COOK$.

Comparative Example C7

In a three-necked, 1000 mL flask, fitted with a condenser, stirrer, and thermometer, were placed 263 g (0.25 mole) $C_8F_{17}SO_2N(CH_2CH_3)H$, 200 g dry DMF, and 109 g of 25% sodium methoxide ($NaOCH_3$, 0.5 mole) in methyl alcohol. All of the methyl alcohol (about 80 g) was distilled off. The reaction mixture was cooled under nitrogen. Then, 0.5 mole (61 g) of methyl-3-chloropropionate (Cl—$CH_2CH_2COOCH_3$) was added. The reaction was heated at 95° C. for 16 hours. GLC analysis indicated a 96% reaction yield of $C_8F_{17}SO_2N(CH_2CH_3)CH_2CH_2COOCH_3$. The ester was washed three times using 500 mL water at 70° C. The fluorochemical phase was separated. Then 150 g isopropyl alcohol, 100 g deionized water, and 42 g KOH were added. The resulting mixture was heated at 70° C. for 6 hours. GLC indicated that all of the ester was hydrolyzed. The mixture was diluted to 10% solids with a solution of 70% by volume water and 30% by volume isopropyl alcohol. The pH was adjusted to 7.5 with 10% $H_2SO_4$.

Comparative Example C8

The procedure and reactants of Comparative Example C6 were used to prepare a fluorochemical surfactant except KOH was replaced by N,N-dimethylamino-propylamine and 1,2-dimethoxyethane was used as solvent. After completion of the reaction, 11.6 g (0.075 mole) diethyl sulfate were added and the reaction mixture heated at 70° C. for one hour. The product, confirmed by H-NMR analysis, was $C_8F_{17}SO_2N(C_2H_5)C_2H_4CONH(CH_2)_3N^+(CH_3)_2C_2H_5$ $C_2H_5SO_4^-$. A 20% solids solution was prepared in a water and isopropyl alcohol solution as described in Comparative Example C6.

Comparative Example C9

A fluorochemical surfactant was prepared following the procedure of Comparative Example C8, except using propanesultone (9.2 g, 0.075 mole) in place of diethyl sulfate. The product, confirmed by H-NMR analysis, was $C_8F_{17}SO_2N(C_2H_5)C_2H_4CONH(CH_2)_3N^+(CH_3)_2$ $(C_3H_6SO_3^-$.

A 20% solids solution was prepared in a water and isopropyl alcohol solution as described in Comparative Example C6.

Comparative Example C10

A fluorochemical surfactant was prepared following the procedure and reactants of Comparative Example C6 except KOH was replaced by 41.2 g (0.075 mole) of Carbowax™ 550 (a methoxypolyethyleneglycol of average molecular weight of 550 available from Union Carbide), p-toluene sulfonic acid was used as catalyst, and no solvent was used. The ethyl alcohol formed in the reaction was collected in a Dean Stark trap. The reaction temperature was 140° C. for 8 hours under a nitrogen atmosphere. The product structure, confirmed by NMR, was $C_8F_{17}SO_2N(C_2H_5)C_2H_4COO$ $(C_2H_4O)_nC_2H_4OCH_3$ where the average n is about 12. A 20% solids solution was prepared in a water and isopropyl alcohol solution as described in Comparative Example C6.

Comparative Example C11

The fluorochemical cationic surfactant of structure $C_8F_{17}SO_2NHC_2H_4N^+(C_2H_5)_2CH_3I^-$ was prepared as described in U.S. Pat. No. 2,759,019, supra.

A 20% solids solution was prepared in a water and isopropyl alcohol solution as described in Comparative Example C6.

Comparative Example C12

The fluorochemical amphoteric surfactant of structure $C_6F_{13}SO_2NHC_3H_6N^+(CH_3)_2CH_2CO_2^-$ was prepared as described in U.S. Pat. No 4,484,990 (Bultman et al.).

A 20% solids solution was prepared in a water and isopropyl alcohol solution as described in Comparative Example C6.

The fluorochemical solutions obtained in Examples 1 to 6 and Comparative Examples C1 to C12 were diluted to 10% solids by dilution with a solution of 70% by volume water and 30% by volume isopropyl alcohol. Further dilutions to 0.01% solids (100 ppm), and 0.05% solids (500 ppm), were done with deionized water. The surface tensions of the resulting solutions were measured and are shown in Table 4.

TABLE 4

| Contains Surfactant of Example | Surfactant class | Surface tension (dynes/cm) at 500 ppm | Surface tension (dynes/cm) at 100 ppm |
|---|---|---|---|
| 1 | anionic | 17.1 | 18.3 |
| 2 | anionic | 16.5 | 16.8 |
| 3 | anionic | 18.5 | 20.3 |
| 4 | anionic | 20.1 | — |
| 5 | anionic | 24.7 | — |
| 6 | anionic | 19.3 | — |
| C1 | nonionic | 17.7 | 18.7 |
| C2 | cationic | 18.1 | 19.7 |
| C3 | amphoteric | 18.1 | 20.6 |
| C4 | anionic | 16.4 | 19.7 |
| C5 | anionic | 20.7 | 24.3 |
| C6 | anionic | 17.5 | 19.9 |
| C7 | anionic | 17.2 | 19.1 |
| C8 | cationic | 18.5 | 20.5 |
| C9 | amphoteric | 18.3 | 20.0 |
| C10 | nonionic | 19.4 | 21.0 |
| C11 | Cationic | 17.5 | 18.1 |
| C12 | amphoteric | 19.4 | 21.0 |

The data show that even at low concentration, good surface tension reductions are obtained with the fluoroaliphatic radical-containing sulfonamido compounds of this invention.

Foam was generated from 200 mL of the 500 ppm solutions used for measuring surface tension. The surfactant solutions were mixed with a Hobart mixer for 3 minutes at medium speed. Foam volume (cubic centimeters of foam) was measured in a graduated cylinder. Foam half-life was measured as the seconds needed to drain 100 mL of solution from the foam. The data are shown in Table 5.

TABLE 5

| Surfactant of Example | Surfactant Class | Foam Volume cm³ | Foam Half-Life |
|---|---|---|---|
| 1 | anionic | 300 | less than 30 sec. |
| 2 | anionic | 300 | less than 30 sec. |
| C4 | anionic | 2600 | 375 sec. |
| C5 | anionic | 1500 | 83 sec. |
| C6 | anionic | 1900 | 245 sec. |
| C7 | anionic | 2200 | 300 sec. |
| C1 | nonionic | 900 | 70 sec. |
| C2 | cationic | 200 | less than 30 sec. |
| C3 | amphoteric | 800 | less than 30 sec. |
| C8 | cationic | 600 | less than 30 sec. |
| C9 | amphoteric | 900 | 35 sec. |
| C10 | nonionic | 400 | less than 30 sec. |
| C11 | cationic | 2600 | 320 sec. |
| C12 | amphoteric | 2400 | 320 sec. |

These results show that solutions comprising the novel compounds of this invention possess low-foaming properties which are desirable in some applications, such as high speed coatings, floor polishes, and photographic emulsions. Only the cationic, nonionic, or amphoteric Comparative Examples possess low-foaming properties comparable to those of the ionic examples of this invention. Surprisingly the anionic Examples 1 and 2 of this invention had much lower foam volume and significantly shorter foam half-life than the anionic Comparative Examples C4 to C7.

Various modifications and alterations of this invention will become apparent to those skilled in the art without departing from the scope or spirit of this invention.

What is claimed is:

1. A fluoroaliphatic radical-containing anionic surfactant sulfonamido compound which comprises a fluoroaliphatic radical-containing sulfonamido group and an ethylenecarbonyl group whose beta ethylene carbon atom is bonded to a sulfur or nitrogen atom which is bonded to a linking group bonded to the nitrogen atom of said sulfonamido group, and the carbonyl carbon atom of said carbonyl is bonded to an anionic hydrophilic polar group comprising at least one carbon, nitrogen, oxygen, or sulfur atom.

2. The fluoroaliphatic radical-containing sulfonamido compound of claim 1 wherein said compound has the formula $$R_f-SO_2N(R)WACH(R')CH(R'')C(O)-Y$$

where $R_f$ is a fluoroaliphatic radical; A is S or NR'''; W is siloxylene, silylene, alkylene, arylene, or combinations thereof; R, R', R'', and R''' are independently hydrogen, lower alkyl, aryl, or combinations thereof, and can contain functional groups, or R and R''' together with the nitrogen atoms to which they are bonded and W, form a ring; and Y is an anionic hydrophilic polar group comprising at least one carbon, nitrogen, oxygen, or sulfur atom.

3. The fluoroaliphatic radical-containing sulfonamido compound of claim 2 wherein R, R', R'', and R''' are independently selected from the group consisting of H, lower alkyl of 1 to 4 carbon atoms, or R and R''' together with the nitrogen atoms to which they are bonded and W, form a substituted piperazine ring.

4. The fluoroaliphatic radical-containing sulfonamido compound of claim 2 wherein said W is $-(CH_2)_n-$, where n is from 1 to 12 and R is hydrogen or lower alkyl.

5. The fluoroaliphatic radical-containing sulfonamido compound of claim 2 wherein said $R_f$ is $C_nF_{2n+1}$ where n is from 4 to 10.

6. The fluoroaliphatic radical-containing sulfonamido compound of claim 2 wherein said N(R)WA is selected from the group consisting of $N(R)CH_2CH_2NH$,

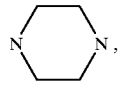

$N(R)CH_2CH_2CH_2Si(CH_3)_2OSi(CH_3)_2CH_2CH_2CH_2NH$,
$N(R)CH(CH_3)CH_2(CH_2CH_2O)_q(CH(CH_3)CH_2O)_zCH_2CH$
$(CH_3)NH$ where q and z are from 1 to 20, and $N(R)$
$CH_2CH_2S$, where R is H, $CH_3$ or $CH_2CH_3$.

7. The fluoroaliphatic radical-containing sulfonamido compound of claim 2 wherein said CH(R')CH(R'') is selected from the group consisting of $CH_2CH_2$, and $C(CO_2M)CH_2$ where M is H, Na, K, Li, or $NH_4$.

8. The fluoroaliphatic radical-containing sulfonamido compound of claim 2 wherein said W is selected from the group consisting of OM, and $N(H)C(CH_3)_2CH_2SO_3M$ where M is H, Na, K, Li, or $NH_4$.

9. The fluoroaliphatic radical-containing sulfonamido compound of claim 2 wherein said compound is

where M is Na, K, Li, H, or $NH_4$.

10. The fluoroaliphatic radical-containing sulfonamido compound of claim 2 wherein said compound is $C_8F_{17}SO_2NHC_2H_4NHC_2H_4CONHC(CH_3)_2CH_2SO_3M$, where M is Na, K, Li, H, or $NH_4$.

11. The fluoroaliphatic radical-containing sulfonamido compound of claim 2 wherein said compound is $C_8F_{17}SO_2N$ $(H)CH_2CH_2N(H)CH_2CH_2C(O)CO_2M$ where M is Na, K, Li, H, or $NH_4$.

12. The fluoroaliphatic radical-containing sulfonamido compound of claim 2 wherein said compound is $C_4F_9SO_2N$ $(H)CH_2CH_2CH_2Si(CH_3)_2OSi(CH_3)_2CH_2-CH_2CH_2N(H)$ $CH_2CH_2C(O)C(CH_3)_2CH_2SO_3M$ where M is H, K, Na, Li, or $NH_4$.

13. The fluoroaliphatic radical-containing sulfonamido compound of claim 2 wherein said compound is $C_8F_{17}SO_2N$ $(H)CH(CH_3)CH_2(CH_2CH_2O)_a-(CH_2CH(CH_3)O)_b$ $CH_2CH(CH_3)N(H)CH_2CH_2C(O)N(H)C(CH_3)_2CH_2SO_3M$ where a and b are from 1 to 20 and M is H, K, Na, Li, or $NH_4$.

14. The fluoroaliphatic radical-containing sulfonamido compound of claim 2 wherein said compound is $C_8F_{17}SO_2N$ $(CH_2CH_3)CH_2CH_2SCH(CO_2M)CH_2CO_2M$ where M is H, K, Na, Li, or $NH_4$.

15. A body of liquid comprising a fluoroaliphatic radical-containing sulfonamido compound, wherein said fluoroaliphatic radical-containing sulfonamido compound comprises a fluoroaliphatic radical-containing sulfonamido group and an ethylenecarbonyl group whose beta carbon atom is bonded to a sulfur or nitrogen atom which is bonded to a linking group bonded to the nitrogen atom of said sulfonadmido group, and wherein an anionic hydrophilic polar group comprising at least one carbon, nitrogen, oxygen, or sulfur atom, is bonded to the carbonyl carbon atom of said ethylenecarbonyl group.

* * * * *

UNITED STATES PATENT AND TRADEMARK OFFICE
CERTIFICATE OF CORRECTION

PATENT NO. : 6,201,122 B1
DATED : March 13, 2001
INVENTOR(S) : Rudolf J. Dams

It is certified that error appears in the above-identified patent and that said Letters Patent is hereby corrected as shown below:

Column 3,
Line 41, "C(R')X(O)Y" should read -- C(R')C(O)Y --;

Column 6,
Line 6, "$CH_2CH_3$" should read -- $CH_2CH_2$ --;

Column 7,
Line 67, "($C_3H_6SO_3$-" should read -- $C_3H_6SO_3$- --;

Column 8,
Line 16, "$(C_2H_4O)_n$" should read -- $(C_2H_4O)_n$ --;
Line 61, second column "Cationic" should read -- cationic --;

Column 9,
Line 13, "①" should read -- 1 --;
Line 14, "②" should read -- 2 --;
Line 39, "anionic surfactant" should be deleted; and Column 10,
Line 22, "W" should read -- L --.

Signed and Sealed this

Sixteenth Day of April, 2002

Attest:

JAMES E. ROGAN
Director of the United States Patent and Trademark Office

Attesting Officer